United States Patent [19]

Watson

[11] 4,259,757

[45] Apr. 7, 1981

[54] SUPPORT CUSHION

[76] Inventor: Robert L. Watson, 14312 Piccadilly Rd., Silver Spring, Md. 20906

[21] Appl. No.: 98,180

[22] Filed: Nov. 28, 1979

[51] Int. Cl.³ .............................................. A47G 9/00
[52] U.S. Cl. ........................................ 5/434; 5/446; 5/433
[58] Field of Search .................................... 5/431–436, 5/446, 465; 269/323–325

[56] References Cited

U.S. PATENT DOCUMENTS

| | | | |
|---|---|---|---|
| 3,139,631 | 7/1964 | Kiefer | 5/432 |
| 3,378,861 | 4/1968 | Lousberg | 5/446 |
| 3,382,510 | 5/1968 | Robinson | 5/435 |
| 3,694,831 | 10/1972 | Treace | 5/435 |
| 3,981,032 | 9/1976 | Brooks | 5/436 |
| 4,017,118 | 4/1977 | Cawley | 5/436 |
| 4,078,376 | 2/1978 | Bond | 5/435 |

*Primary Examiner*—Casmir A. Nunberg
*Attorney, Agent, or Firm*—Roylance, Abrams, Berdo and Farley

[57] ABSTRACT

A support cushion for medical use, especially during surgery, to support the patient's head and neck in convenient positions without patient damage includes two portions made of polyurethane foam separably joined by hook and loop fasteners or the like. The portion normally on top when the two are used together has a hemispherical depression in the top, a groove extending outwardly from the depression, dihedral plane surfaces extending out from the groove and a rectangular bottom surface. The bottom portion has a rectangular top surface, a V-shaped groove in the bottom and planar surfaces on either side of the V-groove lying in a plane which makes an acute angle of about 7° with the plane containing the top.

3 Claims, 7 Drawing Figures

SUPPORT CUSHION

BACKGROUND OF THE INVENTION

It is well known to provide headrests for various purposes and to form such headrests using resilient material such as polymeric foams. Examples of headrests for various specific purposes, including medical and dental, are found in the following patents:

| | |
|---|---|
| 2,940,087 | Kiefer |
| 3,139,631 | Kiefer |
| 3,694,831 | Treace |
| 3,981,032 | Brooks |
| 3,987,507 | Hall |
| 4,017,118 | Cawley |

However, in various circumstances during medical procedures, and particularly during those procedures involving anesthesia, certain problems can arise as a result of anesthetization of the patient with the patient in a supine or lateral position for extended intervals of time. For example, localized occipital pressure with the patient supine can result in ischemic alopecia, and such pressure on the ear in the lateral position can result in necrosis of the ear in varying degrees. As will be apparent, special measures are necessary to avoid such conditions.

It is also important to maintain the patient's head in the proper position for the procedure to be undertaken, depending upon the need for endotracheal intubation, and in ENT procedures a lower and differently shaped rest is needed to limit head rotation and for cervical support. Yet another shape and height of headrest is required for pediatric procedures.

While certain specific headrests have been designed for certain of these objectives, neither the specially designed headrests nor those of general utility have satisfied the needs of the medical profession in this area.

BRIEF DESCRIPTION OF THE INVENTION

Accordingly, it is an object of the present invention to provide a support cushion structure for supporting a patient's head with the patient in the supine or lateral position during operative and post-operative periods.

A further object is to provide such a cushion which properly supports and positions the head for specific procedures and conditions without applying excessive localized pressure which could give rise to disorders associated with decreased blood flow.

Yet another object is to provide a support cushion having surfaces for providing any one of a variety of different kinds of support with the same basic structure.

A still further object is to provide a cushion of foamed polymeric material which provides firm but gentle support and which can be manufactured at reasonable cost.

Briefly described, the invention includes a support cushion, particularly for use in supporting the head and cervical regions of a medical patient, comprising a first unitary cushion portion formed entirely of polymeric foam material and having a rectangular, substantially planar lower surface, means defining a generally hemispherical depression extending inwardly from the upper surface, a generally U-shaped groove extending outwardly from said depression generally parallel with said lower surface, and dihedral planer surfaces extending symmetrically outwardly and upwardly from said groove and depression, a second unitary cushion portion formed entirely of polymeric foam material and having a rectangular, substantially planar upper surface, and a lower surface having planar side portions lying in a plane forming an acute angle with the plane containing said upper surface of said second portion and dihedral surfaces extending symmetrically between the inner margins of said side portions and a line, thereby defining a shallow, V-shaped groove, means for releasably interconnecting said lower surface of said cushion portion and said upper surface of said second cushion position in parallel adjacent relationship.

In order that the manner in which the foregoing and other objects are attained in accordance with the invention can be understood in detail, reference is made to the following drawings, which form a part of this specification, and wherein.

Figure 1:
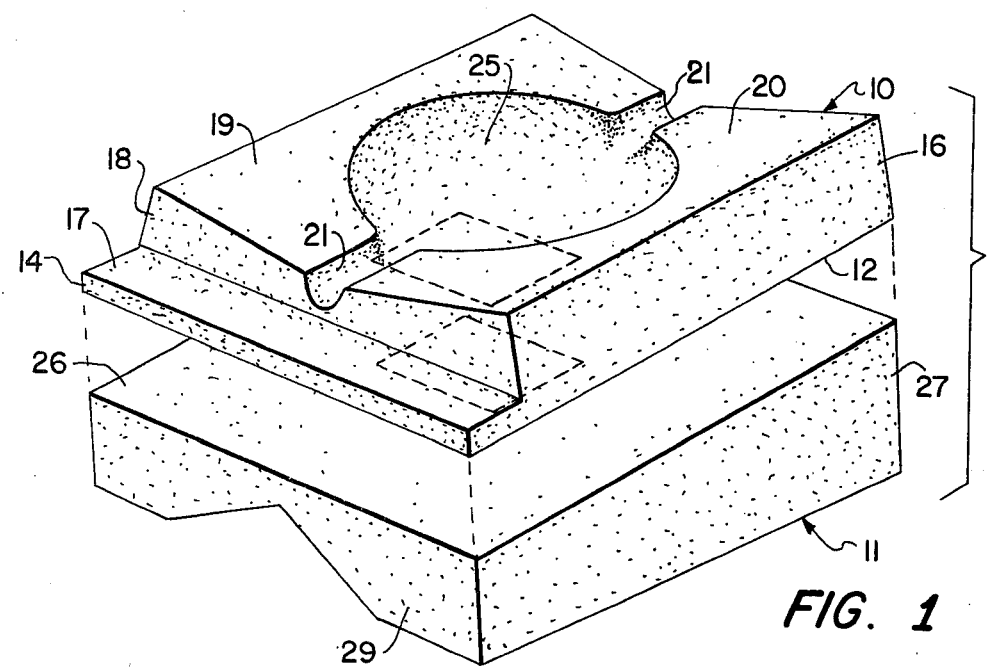
FIG. 1 is an exploded perspective view of a support cushion in accordance with the present invention, showing the two portions thereof slightly separated.

As will be seen in the perspective view of FIG. 1 and in FIGS. 2-5, the support cushion or headrest of the present invention includes an upper cushion portion indicated generally at 10 and a lower cushion portion indicated generally at 11. The upper cushion portion has a planar rectangular bottom surface 12 and an end surface 13 which is perpendicular to the bottom surface, an opposite end surface 14 which is parallel with surface 13, and side surfaces 15 and 16 which converge upwardly and inwardly at an angle of approximately 80° to surface 12. It will be observed that end surface 14 is relatively short, there being a portion cut away to form a horizontal surface 17 which is parallel with surface 12 and a surface 18 which is parallel with surfaces 14 and 13.

The upper surface of cushion portion 10 is defined by two dihedral surface portions 19 and 20 which lie in planes intersecting at a dihedral angle of approximately 155°. These surfaces do not, however, directly meet, the line of junction which would otherwise exist between the surfaces being interrupted by a longitudinal generally U-shaped groove 21 which extends along a bisecting center line of cushion portion 10.

Figure 2:
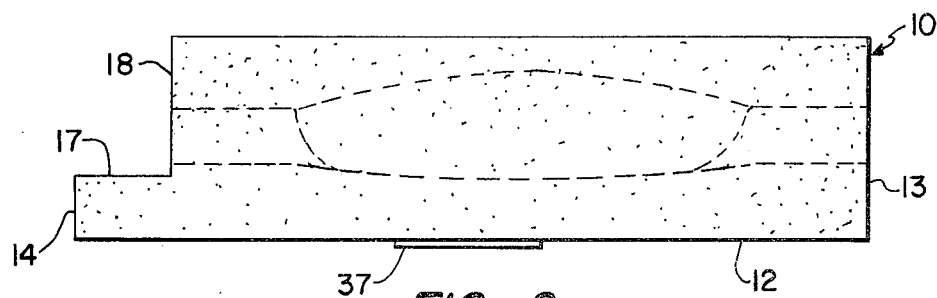
FIG. 2 is a side elevation of the upper portion of the cushion of FIG. 1.
Figure 3:
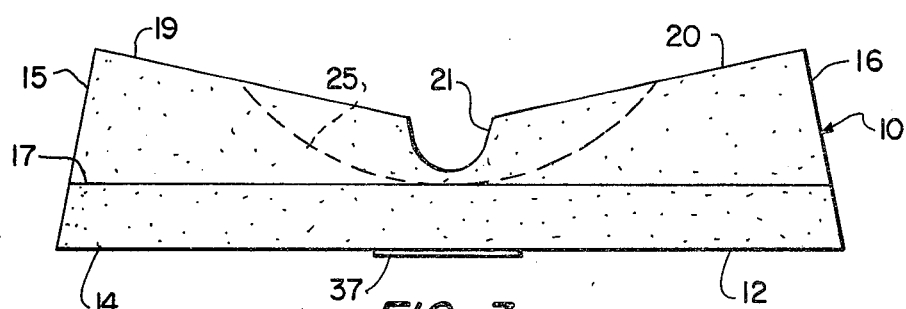
FIG. 3 is a front elevation of the cushion portion of FIG. 2.

As will be recognized from a comparison of FIGS. 1, 2 and 3, the bottom plan view of cushion portion 10 would be a simple rectangle, approximately a square. Similarly, the top plan view of that portion between surfaces 13 and 18 and between the upper edges of surfaces 15 and 16 would be a rectangle approaching a square of smaller area than the lower since sides 15 and 16 slope inward from bottom to top. Centrally located in this upper portion is a generally hemispherical depression 25 the bottom extremity of which extends approximately to the level of surface 17 so that the thickness of that portion between surfaces 12 and 17 is approximately the same as the thickness between surface 12 and the bottom of the depression 25. Depression 25 is formed to receive the head, or a portion thereof, as will be more fully described.

By way of example, cushion portion 10 is advantageously formed such that each edge of surface 12 is approximately 8 inches (20.3 centimeters) long, and the height of portion 10 is approximately 2 inches (5 centimeters). Depression 25 has a diameter of about 10.5 cm. and a depth of about 3 cm.

Cushion portion 11, the bottom portion in FIG. 1, has a somewhat simpler configuration. Portion 11 has an upper surface 26, side surfaces 27 and 28 and end surfaces 29 and 30. It will be observed that cushion portion 11 is shown with surface 26 uppermost in FIG. 1, but that surface 26 is shown as the bottom surface in FIGS. 4 and 5. The reason for this, as will be further described, is that the cushion portions can be used independently of each other and, when used independently, portion 11 would be in the position shown in FIGS. 4 and 5, but when used in conjunction with portion 10 it would occupy the orientation shown in FIG. 1.

Figure 4:
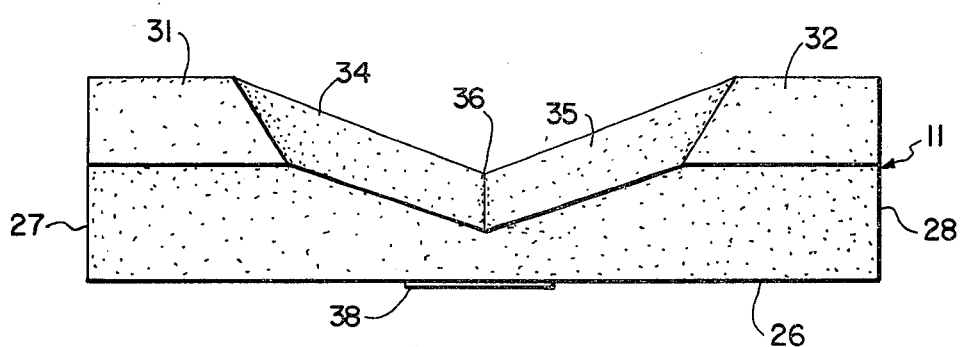
FIG. 4 is an inverted front elevation of the bottom portion of the cushion of FIG. 1.
Figure 5:
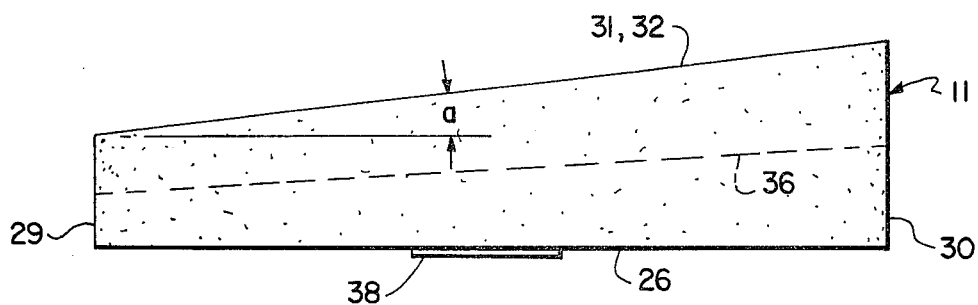
FIG. 5 is a side elevation of the cushion portion of FIG. 4, also inverted relative to FIG. 1.

The lower surface of portion 11 (as shown in FIG. 1, or the upper surface as shown in FIGS. 4 and 5) includes surface portions 31 and 32 which lie in the same plane and adjacent to sides 27 and 28, respectively. The plane containing surfaces 31 and 32 forms an angle a of approximately 7° with surface 26 so that end surface 30 is taller than end surface 29.

Surfaces 31 and 32 are separated from each other by a shallow, V-shaped groove formed by dihedral surfaces 34 and 35 which join at a line 36, line 36 lying at an angle of approximately 3°-4° with respect to surface 26. Thus, surfaces 34 and 35, in true projection, are trapezoidal with the edges along surfaces 29 and 30 being parallel with each other, and the width of the groove increases from surface 29 to surface 30 from about 9.5 cm to about 12.5 cm.

As previously indicated, when cushion portions 10 and 11 are used together surfaces 12 and 26 are placed in adjacent relationship. In order to maintain them in this relationship without slippage, the surfaces can be provided with detachable interconnection means shown as a hook and loop fastener set 37 and 38 (e.g. VELCRO), one half of this set being fastened to each of the surfaces. While the patches of hook and loop fastener fabric are shown disposed in the centers of surfaces 12 and 26, it will be recognized that such patches can be disposed at any location on the surface, and it will also be recognized that other detachable connection means, such as double-sided tape, can be employed.

Having described the structural arrangement of the support cushion of the invention, the use thereof will be described in general terms. As previously indicated herein, there are several fundamental problems related to the position of the supine patient's head in the operative and post-operative periods, and these are dealt with by the present invention. If the patient is not to be intubated, as when an anesthetic is to be administered by mask, the positional alignment of the airway axes is critical to the maintenance of the breathing passage. In this connection, three specific axes of the human anatomy are referred to, one being the axis of the larynx, the second being the axis of the mouth and the third being the axis of the pharynx. The need for aligning specific ones of these axes depends upon whether the patient is to have his trachea (windpipe) intubated or not.

Figure 6:
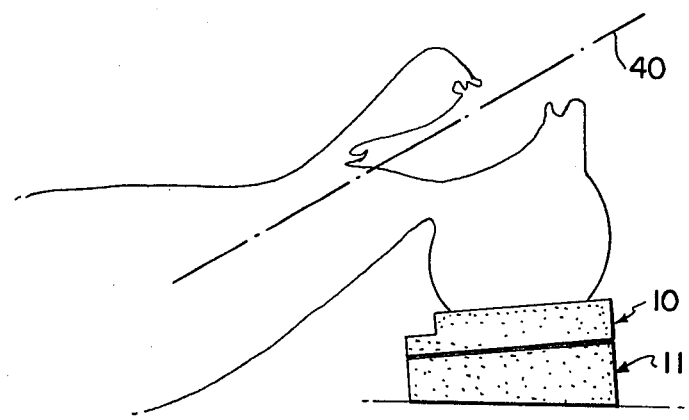
FIGS. 6 and 7 are views showing patient head positions on the cushion of FIGS. 1-5 in the intubated and unintubated conditions, respectively.

FIG. 6 illustrates the position in which the patient's cervical and head region should be oriented for endotracheal intubation. Positional alignment of all three airway axes should be optimal to allow easy visualization of the larynx and intubation of the trachea. Thus, the axis indicated at 40 in FIG. 6 shows the approximate line along which all three of the axes previously mentioned (and shown in FIG. 7) are aligned for intubation. This is achieved with the support cushion of the present invention because the hemispherical depression 25 in the upper portion of cushion portion 10 can receive the upper portion of the head and hold it in a secure position, and because of the 7° inclination of the upper surface of the cushion portion 11 which, when the two cushions are used together, inclines the support portions of the upper cushion. This inclination is a particularly important and significant aspect of the invention, in combination with recess 25, because of the criticality of alignment of the anatomical axes described above. The advantages of improved positioning attained by the present invention as compared with prior devices such as that shown in the patent to Treace have been clearly demonstrated using X-ray techniques.

Figure 7:
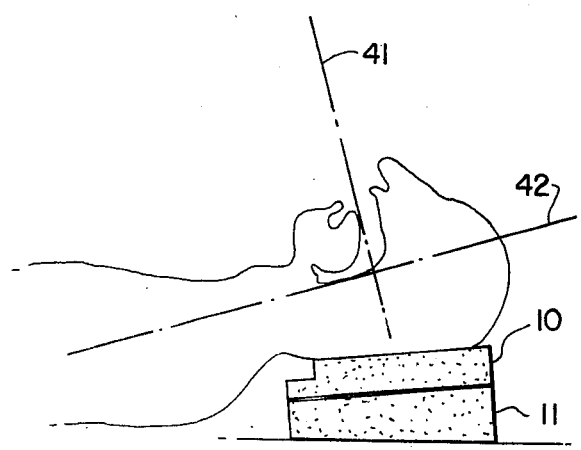

For maintenance of an airway in the unintubated patient, the axis of the mouth, indicated at 41 in FIG. 7, is generally perpendicular to the axis of the pharynx, but the axes of the pharynx and larynx should be aligned with each other as shown at 42 in FIG. 7. Again, this proper axial positioning is facilitated by the hemispherical recess and the inclination.

Also as previously indicated, support of the patient's head by a traditional flat cushion, or by a cushion having excessively firm surface portions, has resulted in postoperative alopecia due to ischemia in the area of contact pressure, especially when this contact was continued during low blood flow states. The hemispherical depression 25 permits the distribution of support over a large region of the head, minimizing the impairment of the microcirculation in any one area. The existence of the groove formed by surfaces 34 and 35 also contributes to this effect because the void permits a yielding directly under the point of greatest load.

Additionally, when a patient is turned from the supine to the lateral position with the head resting on a flat cushion or the like, the entire weight of the head is borne by the ear with a similar potential for impairment of the microcirculation. With the ear placed in depression 25, a majority of the support pressure is applied over the peri-auricular area. This minimizes the likelihood of auricular necrosis.

It is particularly significant to note that each of cushion portions 10 and 11 is unitarily formed from relatively soft and light foamed polyurethane and that no laminae are used on any exposed surfaces, especially patient-contacting surfaces. By "unitarily formed" it is meant that each cushion portion is formed as a single entity from a single piece of foamed material, or each cushion portion is foamed in a mold to the desired shape as a single entity, no gluing being involved.

As previously indicated, the cushion portions 10 and 11 can be used separately for specific purposes. This is a considerable advantage for the practicing physician because it permits him, or a hospital, to stock a single set of articles capable of performing multiple functions, tending to minimize inventory. Cushion portion 10 can be separately used as a pediatric headrest, the height thereof (approximately 5 cm. overall) being correct for that purpose. The flange having surfaces 14 and 17 acts as a partial cervical support in that use.

Cushion portion 11, as previously indicated, can be used in the position shown in FIGS. 4 and 5 as a head and cervical support for eye, ENT and certain oral surgical procedures. When so used, the patient's shoulders are at the end which is lowest, i.e., adjacent surface 29. In this use, the V-shaped groove is quite effective to prevent lateral head rotation.

Furthermore, portion 11 used above is particularly well suited for supporting the head in a lateral position at a relatively low and declined orientation for procedures such as ear surgery (where operating microscopes are to be used above the head), the angle of the head being much better than with prior supports or with both of portions 10 and 11 used together. In this use, the lower ear only receives periauricular pressure as it lies in the bottom of the groove and thus protects the ear which lies in depression 25.

The preferred foam material to be used in making the support cushion described herein is an ether derivative polyurethane foam having a density of about 1.5 lb per cubic foot as determined by the conventional indentation load deflection formula in which a reading of 25 to 30 lb. per 50 square inches is obtained.

While certain advantageous embodiments have been chosen to illustrate the invention it will be understood by those skilled in the art that various changes and modifications can be made therein without departing from the scope of the invention as defined in the appended claims.

What is claimed is:

1. A support cushion, particularly for use in supporting the head and cervical regions of a medical patient, comprising a first unitary cushion portion formed entirely of polymeric foam material and having
    a rectangular, substantially planar lower surface,
    means defining a generally hemispherical depression extending inwardly from the upper surface,
    a generally U-shaped groove extending outwardly from said depression generally parallel with said lower surface, and
    dihedral planar surfaces extending symmetrically outwardly and upwardly from said groove and depression;

a second unitary cushion portion formed entirely of polymeric foam material and having
    a rectangular, substantially planar upper surface, and
    a lower surface having planar side portions lying in a plane forming an acute angle with the plane containing said upper surface of said second portion and
    dihedral surfaces extending symmetrically between the inner margins of said side portions and a line, thereby defining a shallow, V-shaped groove;

means for releasably interconnecting said lower surface of said first cushion portion and said upper surface of said second cushion portion in parallel adjacent relationship.

2. A support cushion according to claim 1 wherein said means for releasably interconnecting includes hook and loop fastener material.

3. A support cushion according to claim 1 wherein the angle between the planes containing said lower surface and said upper surface and said upper surface in said second cushion portion is about 7°.

* * * * *